United States Patent [19]
Lezdey et al.

[11] Patent Number: 6,096,327
[45] Date of Patent: Aug. 1, 2000

[54] COSMETIC COMPOSITIONS CONTAINING HUMAN TYPE SERINE PROTEASE INHIBITORS FOR REVITALIZING THE SKIN

[75] Inventors: John Lezdey, Voorhees, N.J.; Allan Wachter, Tempe, Ariz.

[73] Assignee: Protease Sciences Inc., Clearwater, Fla.

[21] Appl. No.: 09/186,989

[22] Filed: Nov. 5, 1998

[51] Int. Cl.[7] .................................................. A61K 7/48
[52] U.S. Cl. ..................... 424/401; 424/64; 424/DIG. 5; 514/8; 514/12; 514/21
[58] Field of Search ................. 424/401, 64, DIG. 5; 514/844, 845, 846, 8, 12, 21

[56] References Cited

U.S. PATENT DOCUMENTS

| | | | |
|---|---|---|---|
| 5,118,707 | 6/1992 | Chatterjee et al. | 514/469 |
| 5,190,914 | 3/1993 | Lezdey et al. | 514/12 |

*Primary Examiner*—Jyothsna Venkat

[57] ABSTRACT

Cosmetic compositions and methods are provided for revitalizing the skin especially where it is placed in an environment which can cause injury to the skin. The compositions contain an effective amount of a protease inhibitor to provide a prophylactic or repairing effect.

8 Claims, No Drawings

COSMETIC COMPOSITIONS CONTAINING HUMAN TYPE SERINE PROTEASE INHIBITORS FOR REVITALIZING THE SKIN

FIELD OF THE INVENTION

The present invention relates to cosmetic compositions containing human type serine protease inhibitors. More particularly, there is provided cosmetic compositions containing anti-chymase, anti-tryptase and/or anti-elastase protease inhibitors which improves or revitalizes atmosphere damaged skin including chapped lips, wind burn, sun burn and wrinkles resulting therefrom, as well as natural skin eruptions.

BACKGROUND OF THE INVENTION

Alpha 1-antichymotrypsin is a plasma protease inhibitors synthesized in the liver. It is a single glycopeptide chain of approximately 68,000 daltons and belongs to a class of serine protease inhibitors with an apparent affinity toward chymotrypsin-like enzymes. Alpha 1-antichymotrypsin is structurally related to alpha 1-antitrypsin.

Alpha 2-macroglobulin is a glycoprotein containing 8–11% carbohydrate which can be isolated from plasma by gel filtration chromatography.

Alpha 1-proteinase inhibitor (alpha 1-antitrypsin) is a glycoprotein having a molecular weight of 53,000 determined by sedimentation equilibrium centrifugation. The glycoprotein consists of a single polypeptide chain to which several oligosaccharide units are covalently bonded. Human alpha-1 proteinase inhibitor has a role in controlling tissue destruction by endogenous serine proteinases. A genetic deficiency of alpha-1 proteinase inhibitor, which accounts for 90% of the trypsin inhibitory capacity in blood plasma, has been shown to be associated with the premature development of pulmonary emphysema. The degradation of elastin associated with emphysema probably results from a local imbalance of elastolytic enzymes and the naturally occurring tissue and plasma proteinase inhibitors. Alpha-1 proteinase inhibitor inhibits human pancreatic and leukocyte elastases. See Pannell et al, Biochemistry. 13, 5339 (1974); Johnson et al, Biochem, Biophys. Res. Commun., 72 33 (1976); Del Mar et al, Biochem. Biophys. Res. Commun., and Heimburger et al, Proc. Int. Res. Conf. Proteinase Inhibitors. 1st, 1–21 (1970).

SUMMARY OF THE INVENTION

The present invention provides a topical cosmetic composition for improving or revitalizing the texture of skin or as a prophylactic against skin irritations or degradations. The composition is especially useful for treating skin damaged by the atmosphere such as sun damaged or wrinkled skin, chapped lips or skin on face and hands, and for treatment after a chemical peel, for example with a hydroxy glycollic acid or to prevent skin eruptions.

The human type serine protease inhibitors which can be used in the present invention include natural or recombinant alpha 1-antitrypsin, alpha 1-antichymotrypsin, secretory leucocyte protease inhibitor (SLPI), alpha 2-macroglobulin, c-reactive protein, CI-esterase inhibitor and alpha 2-antiplasmin. The most preferred are alpha 1-antitrypsin and alpha 1-antichymotrypsin used alone or in combination.

The wound healing properties of alpha 1-antitrypsin are helpful in cosmetic preparations which are intended to cover blemishes or skin eruption.

The compositions of the invention contain at least about 0.5 percent of the protease inhibitors. The amount of protease inhibitor which generally can be used is about one percent by weight, preferably, about 1 to 10% by weight of composition. Greater amounts can be utilized but are not required to achieve the desired results.

The compositions of the invention can be used in the form of a lotion, creme, gel or solution, depending on the use or treatment contemplated. The extract can be formulated into cosmetic compositions such as lipsticks, hand cremes, after sun compositions, and the like.

The protease inhibitors can be used alone or with other skin treatment compounds such as aloe vera.

It is a general object of the invention to provide a cosmetic composition which contains an effective amount of the protease inhibitor to improve the quality of the skin.

It is another object to provide a cosmetic composition for treating sensitive skins.

It is yet another object to provide a topical composition which helps revitalize environmentally damaged skin.

It is a still further object of the invention to provide a method for improving damaged skin and preventing its occurrence.

DESCRIPTION OF THE PREFERRED EMBODIMENTS

The present invention provides an improvement in cosmetic compositions by providing safe and natural chymase, tryptase and/or elastase inhibitors which are non-irritating to human skin. The anti-viral characteristic of alpha 1-antitrypsin and SLPI are useful in compositions which can transmit viral infections from one user to another exposed to viral infection.

The favorable cosmetic activity of the protease inhibitors is believed to be the results of the chymase, tryptase and elastase inhibition by the protease inhibitors before or during inflammation. Also, the control of the elastase permits the laying down of new tissue without degradation resulting from the presence of the combination of excess elastase and Cathepsin G. After a chemical peel or removal of the upper dermal layer mechanically or naturally, the new tissue layer which is layed down is more resilient and thereby reduces the wrinkles unless scarring or degradation occurs due to excess elastase or cathepsin G. In aging skin, the protease inhibitor appears to revitalize as well as soften the existing skin. The compositions with the protease inhibitor have a prophylactic effect and reduce the incidence of skin eruptions or inflammations as a result of the action against serine proteases or mast cell involvement.

The compositions according to the invention may be presented in all forms normally used for topical application, in particular in the form of aqueous, aqueous-alcoholic or, oily solutions, or dispersions of the lotion or serum type, or anhydrous or lipophilic gels, or emulsions of liquid or semi-solid consistency of the milk type, obtained by dispersing a fatty phase in an aqueous phase (O/VV) or vice versa (VV/O), or of suspensions or emulsions of soft, semi-solid consistency of the cream or gel type, or alternatively of microemulsions, of microcapsules, of microparticles or of vesicular dispersions to the ionic and/or nonionic type. These compositions are prepared according to standard methods.

They may also be used for the scalp in the form of aqueous, aqueous-alcoholic solutions, or in the form of creams, gels, emulsions or foams or alternatively in the form of aerosol compositions also containing a propellant agent under pressure.

The amounts of the different constituents of the compositions according to the invention are those traditionally used in the cosmetic field.

These compositions constitute, in particular, cleansing, protective, treatment or skin care creams for the face, hands, feet, major anatomical folds or the body (for example day creams, night creams, make-up removal creams, foundation creams, sun-protection creams), fluid foundations, make-up removal milks, protective or skin care body milks, after-sun milks, skin care lotions, gels or foams, such as cleansing or disinfecting lotions, bath compositions, deodorant compositions, aftershave gels or lotions, compositions for treating certain skin disorders such as those mentioned above.

The sun can produce a series of lesions on the skin which can be precancerous (e.g. seborrheic, keratoses or actinic keratoses).

The compositions according to the invention may also consist of solid preparations constituting cleansing bars or soaps.

The compositions may also be packaged in the form of an aerosol composition containing a propellant agent under pressure.

When the composition of the invention is an emulsion, the proportion of the fatty phase can range from 5% to 80% by weight, and preferably from 5% to 50% by weight, relative to the total weight of the composition. The oils, emulsifiers and coemulisifiers used in the composition in emulsion form are chosen from those traditionally used in the cosmetics. The emulsifier and the coemulsifier are present in the composition in a proportion ranging from 0.3% to 30% by weight, and preferably 0.5 to 30% or, better still, from 0.5 to 20%, by weight relative to the total weight of the composition. The emulsion can, in addition, contain lipid vesicles.

When the compositions of the invention is an oily gel or solution, the fatty phase can represent more than 90% of the total weight of the composition.

In a known manner, the composition of the invention may also contain adjuvants which are customary in the cosmetics, such as hydrophilic or lipophilic gelling agents, hydrophilic or lipophilic active agents, preservatives, antioxidants, solvents, perfumes, fillers, screening agents, bactericides, odor absorbers and coloring matter. The amounts of these different adjuvants are those traditionally used in the cosmetic, or dermatological field, and are, for example, from 0.01% to 10% of the total weight of the composition. Those adjuvants, depending on their nature, may be introduced into the fatty phase, into the aqueous phase and/or into lipid spherules.

As oils which can be used in the invention, mineral oils (liquid paraffin), vegetable oils (liquid fraction of shea butter, sunflower oil), animal oils (perhydrosquatene), synthetic oils (Purcellin oil), silicone oils (cyclomethicone) and fluorinated oils (perfluoro polyethers) may be mentioned.

Fatty alcohols, fatty acids (stearic acid) and waxes (paraffin, carnauba, beeswax) may also be used as fatty substances.

As emulsifiers which can be used in the invention, glycerol stearate, polysorbate 60 and the PEG-6/PEG-32/glycol stearate mixture sold under the name Tefose® 63 by the company Gattefosse may be mentioned as examples.

As hydrophilic gelling agents, carboxyvinyl polymers (carbomer), acrylic copolymers such as acrylate/alkylacrylate copolymers, polyacrylamides, polysaccharides such as hydroxypropylcellulose, clays and natural gums may be mentioned, and as lipophilic gelling agents, modified clays such as bentones, metal salts of fatty acids such as aluminum stearates and hydrophobic silica, or alternatively ethylcellulose and polyethylene may be mentioned.

As hydrophilic active agents, proteins or protein hydrolysates, amino acids, polyols, urea, allanloin, sugars and sugar derivatives, water-soluble vitamins, starch and plant extracts, in particular those of Aloe vera may be used.

As lipophilic active, agents, retinol (vitamin A) and its derivatives, tocopherol (vitamin E) and its derivatives, essential fatty acids, ceramides and essential oils may be used. These agents add extra moisturizing or skin softening features when utilized.

The compositions of the invention may include other plant or herbal extracts. For example, there may be utilized extracts of Paraguay tea, Kola and Guarana, which provide a source of methylxanthines, saponius, tannins and glycosides that have been shown to reduce swelling and redness. The extract of Paraguay tea is known as "Mate extract" and is described in the "International Cosmetic Ingredient Dictionary", 5th Edition. Mate extract is commercially available in combination with extracts of Kola and Guarana which is sold by Cosmetic Ingredient Resources of Stamford, Conn. under the trademark "QUENCHT."

Each of mate extract, serine protease inhibitor and aloe vera extract are known to provide anti-inflammatory activity. The anti-elastase and anti-tryptase activity of the protease inhibitor has been shown to provide a synergistic effect in treating skin inflammations including sun burn.

A surfactant can be included in the composition so as to provide deeper penetration of the ingredients. Although natural surfactants are preferred, others such as isopropyl myristate can be used.

U.S. Pat. Nos. 4,916,117; 5,215,965; 5,093,316; 5,217,951, which are herein incorporated by reference, disclose the anti-inflammatory characteristics of serine protease inhibitors.

Alpha 1-antitrypsin and alpha 2-macroglobulin have been demonstrated as having anti-viral activity against a wide variety of viruses including HIV and Herpes Simplex.

Since it is quite common that the same cosmetic compositions are often utilized by more than one person so that disease can be spread, it is advantageous to provide a cosmetic composition which possesses anti-viral characteristics. This need exists in both lipsticks and eyeliners or eye shadows.

The following examples illustrating the compositions of the invention are not intended to limit the scope of the invention. The amounts indicated are by weight percent unless otherwise noted.

EXAMPLE 1

A gel is prepared by admixing the following ingredients.

| Ingredient | Wt % |
| --- | --- |
| Carbomer 940 | 4.10 |
| Xantham gum | 0.15 |
| Propylene glycol | 51.94 |
| Dipropylene glycol | 10.00 |
| Ethoxydiglycol | 15.00 |

| Ingredient | Wt % |
| --- | --- |
| Dimethylisosorbide | 10.00 |
| Aloe Vera gel | 8.00 |
| Surfactant | 0.05 |
| Alpha 1-antitrypsin | 1.76 |
| | 100% |

This composition is useful to reduce wrinkles or after a chemical skin peel.

In lieu of alpha 1-antitrypsin, alpha 1-antichymotrypsin can be utilized alone or in combination with alpha 1-antitrypsin.

EXAMPLE 2

A gel is prepared by admixing the following ingredients:

| Ingredient | Wt % |
| --- | --- |
| 1. Propylene Glycol | 51.94 |
| 2. Carbomer 940 | 2.10 |
| 3. Dipropylene glycol | 10.00 |
| 4. Xanthan gum | 0.15 |
| 5. Ethoxydiglycol | 15.00 |
| 6. Dimethylisosorbide | 10.00 |
| 7. Ascorbic Acid | 2.00 |
| 8. Chloroxylenol | 0.20 |
| 9. Linoleamidopropyl PG-diammonium chloride phosphate | 1.50 |
| 10. Glycereth 4.5 Lactate | 2.00 |
| 11. Aloe Vera Gel | 2.00 |
| 12. Alpha 1-antitrypsin | 2.00 |
| 13. Tetrasodium EDTA | 0.10 |
| 14. Citric Acid | 0.010 |
| 15. Cocamidopropyl PG-dimonium chloride phosphate | 1.00 |

Ingredients 1 and 2 are mixed to disperse and form a gel. About 80% of ingredient 3 is mixed with ingredient 4, added to the gel and slightly heated with admixture. The balance of 3 is mixed with ingredients 5–10 and added to the gel. Ingredients 11–15 are then admixed and added to the gel at 38 degrees C. After mixing, the gel is brought to room temperature.

This gel composition can be used as an after-sun treatment.

EXAMPLE 3

A lotion is prepared by admixing the following ingredients:

| Ingredient | Wt % |
| --- | --- |
| Propylene Glycol Stearate | 9.50 |
| Isocetyl alcohol | 5.00 |
| PEG-100 Stearate | 1.20 |
| Water | 69.90 |
| Methyl paraben | 0.20 |
| Propylene glycol | 13.10 |
| Sorbitan palmitate | 0.60 |
| Alpha 1-antitrypsin | 6.00 |
| Mate extract | 0.50 |
| | 100% |

The lotion can be used to treat chapped hands.

EXAMPLE 4

An anti-wrinkle cream is prepared by mixing the following ingredients:

| Ingredient | Wt % |
| --- | --- |
| Glycerol stearate | 8.0 |
| PEG-100 stearate | 2.0 |
| Cetostearyl alcohol | 2.5 |
| Disodium EDTA | 0.1 |
| Methyl Paraben | 0.1 |
| Propylene glycol | 6.0 |
| Sorbitan stearate | 0.7 |
| Alpha 1-antitrypsin | 2.5 |
| Aloe vera gel | 5.0 |
| Water | 13.5 |
| | 100% |

EXAMPLE 5

An after-sun composition is prepared by admixing the following ingredients:

| Ingredient | Wt % |
| --- | --- |
| Carbomer | 2.80 |
| Propylene Glycol | 40.05 |
| Disodium EDTA | 1.10 |
| Methyl Paraben | 0.20 |
| Alpha 1-antitrypsin | 2.00 |
| Alpha 1-antichymotrypsin | 2.00 |
| Mate extract | 0.35 |
| Aloe Vera Gel | 52.50 |
| | 100% |

EXAMPLE 6

A solution according to the invention is prepared by admixing the following ingredients:

| Ingredient | Wt % |
| --- | --- |
| Ethoxyglycol | 15.00 |
| Propylene Glycol | 35.00 |
| Water | q.s. |
| Disodium EDTA | 0.10 |
| Alpha 1-antitrypsin | 4.50 |
| Aloe Vera Gel | 36.75 |
| | 100% |

EXAMPLE 7

A shampoo is prepared by admixing the following ingredients:

| Ingredient | Wt % |
| --- | --- |
| C12–15 Pareth-7 Carboxylic Acid | 10.0 |
| Isosteareth -6 Carboxylic Acid | 5.0 |
| Hexylene Glycol | 8.0 |

-continued

| Ingredient | Wt % |
| --- | --- |
| Chloroxylenol | 0.5 |
| Alpha 1-antitrypsin | 2.0 |
| Mate Extract | 0.5 |
| Aloe Vera Gel | 2.0 |
| Na2 EDTA | 0.1 |
| Water | 71.9 |
| | 100% |

The shampoo is useful in the treatment of scalp inflammation or itch.

The shampoo can be used for sensitive scalps which have sensations of purities, that is to say by itching or prickling to different factors such as inflammation triggered by local factors such as soaps, surfactants, erythema, and the like.

EXPERIMENT 1

5 adults over 50 years of age for one week were exposed to the summer sun, swam in a fresh water lake and did not utilize a sunscreen during the day. At the end of each day, each adult applied a commercial suntan lotion (Coppertone®) to one half of the face and to the other half applied the composition of Example 4.

At the end of one week, the faces were examined. On each adult the part of the face which was treated with suntan lotion had a noticeable increase in wrinkles around the eyes and some erythema. The side of the face on which the composition of Example 4 was applied had a reduction in the depth of the wrinkles, the skin was smoother and not erythemous. The greater and more numerous the wrinkles before hand, the greater the visible effect of the treatment.

After three weeks without the use of suntan lotion or the alpha 1-antitrypsin composition, skin peeling occurred over a greater part of the face wherein suntan lotion was applied.

What is claimed is:

1. A method for revitalizing skin and reducing wrinkles in the skin which comprises topically administering a composition containing an effective amount of a human serine protease inhibitor to provide an anti-elastase, anti-chymase or anti-tryptase treatment to the skin and a suitable cosmetic carrier.

2. The method of claim 1 wherein said composition contains at least 0.5 percent by weight of said protease inhibitor.

3. The method of claim 2 wherein said composition contains about 1 to 10% by weight of said protease inhibitor.

4. The method of claim 1 wherein said composition is in the form of a lotion, cream of gel.

5. The method of claim 1 wherein said protease inhibitor is selected from the group consisting of alpha 1-antitrypsin and secretory leucocyte protease inhibitor.

6. The method of claim 5 wherein said protease inhibitor is alpha 1-antitrypsin.

7. The method of claim 1 wherein said carrier comprises aloe vera.

8. A method for revitalizing human skin which has been subjected to a chemical peel which comprises topically administering an effective amount of alpha 1-antitrypsin in a suitable cosmetic carrier to the site of the chemical peel.

* * * * *